United States Patent
Burzell

(10) Patent No.: US 11,457,631 B2
(45) Date of Patent: Oct. 4, 2022

(54) ANTIMICROBIAL COMPOUNDS AND METHODS OF USE

(71) Applicant: AEQUOR, INC., Encinitas, CA (US)

(72) Inventor: Cynthia K. Burzell, Encinitas, CA (US)

(73) Assignee: Aequor, Inc., Encinitas, CA (US)

(*) Notice: Subject to any disclaimer, the term of this patent is extended or adjusted under 35 U.S.C. 154(b) by 0 days.

(21) Appl. No.: 16/311,294

(22) PCT Filed: Jun. 28, 2017

(86) PCT No.: PCT/US2017/039783
§ 371 (c)(1),
(2) Date: Dec. 19, 2018

(87) PCT Pub. No.: WO2018/005659
PCT Pub. Date: Jan. 4, 2018

(65) Prior Publication Data
US 2020/0060280 A1 Feb. 27, 2020

Related U.S. Application Data

(60) Provisional application No. 62/355,825, filed on Jun. 28, 2016.

(51) Int. Cl.
| | |
|---|---|
| A01N 57/28 | (2006.01) |
| A01N 31/02 | (2006.01) |
| A01N 57/12 | (2006.01) |
| C07C 305/08 | (2006.01) |
| C07F 9/09 | (2006.01) |

(52) U.S. Cl.
CPC ............ *A01N 57/28* (2013.01); *A01N 31/02* (2013.01); *A01N 57/12* (2013.01); *C07C 305/08* (2013.01); *C07F 9/09* (2013.01); *C07F 9/096* (2013.01)

(58) Field of Classification Search
None
See application file for complete search history.

(56) References Cited

U.S. PATENT DOCUMENTS

| 2,939,876 A * | 6/1960 | Cramer | C07F 9/113 |
| | | | 558/130 |
| 3,004,838 A | 10/1961 | Larson | |
| 2002/0022607 A1 | 2/2002 | Besterman et al. | |
| 2009/0203556 A1 | 8/2009 | Ghesner | |

FOREIGN PATENT DOCUMENTS

| EP | 0102324 | 3/1984 |
| JP | 2004-051719 A | 2/2004 |
| WO | WO2017151663 A1 | 9/2017 |

OTHER PUBLICATIONS

Wozniak et al. Journal of Organic Chemistry, Year:1992, 57(22), 6057-60.*
Abstract—Segall et al. Tetrahedron Letters, vol. 23, Year: 1982, 139.*
Pal et al. Organic & Biomolecular Chemistry (2014), 12(48); 9760-9763.*
Extended European Search Report dated Feb. 20, 2020 for European Patent Application No. 17821159.5, 15 pages.
Cade et al, "Interaction of carboxylic acids with phosphorus trichloride, or butyl phosphorodichloridite, or the chloridite in the absence, and in the presence of pyridine", Journal of Chemical Society, pp. 2030.
The Partial Supplementary European Search Report dated Oct. 17 2019 for European Patent Application No. 17821159.5, 17 pages.
Machado, "Acyl transfer reactions in dipolar aprotic medium: desolvated phosphate ion as acyl acceptor in the formation of energy-rich phosphate compounds", Chemical communications, No. 19, Jan. 1, 1997, pp. 1917.
Pal et al, "Synthesis of coenzyme A thioester using methyl acyl phosphates in an aqueous medium", Organic and Biomolecular Chemistry, vol. 12, No. 48, Jan. 1, 2014, pp. 9760-9763.
European Office Action dated Mar. 11, 2021 for European Patent Application No. 17821159.5, a counterpart foreign application of U.S. Appl. No. 16/311,294, 4 pages.
European Office Action dated Oct. 14, 2020 for European Patent Application No. 17821159.5, a counterpart foreign application of U.S. Appl. No. 16/311,294, 4 pages.
Partial European Search Report dated Mar. 3, 2022 for European Patent Application No. 21214369.7, 18 pages.
Hudson et al., "An approach to the development of organophosphorus fungicides", Phosphorus, Sulfur and Silicon and the Related Elements, vol. 109, No. 1-4, Jan. 1, 1996, pp. 345-348, Abstract, 2 pages.
Jacob, "On the influence of phospheric ester groups in geranyldiphosphate", Bulletin De La Societe Chimique De France, vol. 127, No. 6, Jan. 1, 1990, pp. 719-733.
PPG Industries Inc., "Carbodiimide compounds, polymers containing same coating compositions containing said polymers", U.S. Pat. No. 5,105,010A, Jan. 1, 1992, XP055887396, Abstract, 2 pages.
Takahi et al., "Organic phosphate fungicides for rice", JPS4828058B, Jan. 1, 1973, XP055887402, Abstract, 3 pages.
Extended European Search Report dated Jun. 3, 2022 for European Patent Application No. 21214369.7, 14 pages.

* cited by examiner

*Primary Examiner* — Ana Z Muresan
(74) *Attorney, Agent, or Firm* — Lee & Hayes, P.C.

(57) ABSTRACT

Organophosphorus or organosulfur compounds and methods of using the compounds as cleaning agents, particle dispersants, or surfactants, or to remove, disperse or inhibit the growth of a biofilm, or inhibit the growth of, or kill a fungus or bacteria are provided.

14 Claims, No Drawings

ANTIMICROBIAL COMPOUNDS AND METHODS OF USE

CROSS REFERENCE TO RELATED APPLICATION

This application is a national stage application under 35 U.S.C. § 371 of International Application No. PCT/US2017/039783, filed Jun. 28, 2017, which claims the benefit of U.S. Provisional Application No. 62/355,825, filed Jun. 28, 2016, the disclosures of each of which are explicitly incorporated by reference herein.

BACKGROUND OF THE DISCLOSURE

Microbial biofilms cause systemic infections in plants and animals, including humans, and cause costly marine and industrial related damage and inefficiency. They cost billions of dollars yearly in equipment damage, product contamination, energy losses and medical infections.

All living and non-living surfaces are potential sites for microbial biofilm formation. In the human body biofilms can be associated with tissues (e.g., inner ears, teeth, gums, lungs, heart valves and the urogenital tract) and on indwelling medical devices (e.g., contact lenses, central venous catheters and needleless connectors, endotracheal tubes, intrauterine devices, mechanical heart valves, pacemakers, peritoneal dialysis catheters, prosthetic joints, tympanostomy tubes, urinary catheters, and voice prostheses). An estimated 80% of all microbial infections involve biofilms.

Biofilms are a problem in the water service utilities and many industrial processes including the food, pharmaceutical, paint, oil and gas, and pulp and paper processing, and manufacturing, and engineering industries. Biofilms also cause accelerated corrosion, scale, and slime in industrial systems, oil souring and biofouling. Biofouling of ships' hulls is a major problem for shipping worldwide, causing hydrodynamic drag that requires over 50% additional fuel consumption to overcome, with corresponding increased noxious emissions.

Biofilms are a problem in consumer products including, cleaning products, soaps, lotions, cosmetics, etc. Biofilms result in contamination of the product by microorganisms resistant to the preservatives commonly used in cosmetics. Biofilm contamination can occur at the manufacturing plant or after the product enters the consumer's home.

Biofilms are extremely difficult to remove with existing technology because they can withstand high temperature (>150° C.), biocides, anti-infective compounds including antibiotics, and host immune responses. Also, the huge doses of antimicrobials required to rid systems of biofilm bacteria are environmentally undesirable and medically impractical. The overuse of biocides and antibiotics has triggered the emergence of antimicrobial resistant strains, all of which are biofilm-formers (e.g., MRSA [methicillin-resistant *Staphylococcus aureus*). Thus, there is an immediate need for safe and effective products that combat biofilms.

SUMMARY

The present disclosure is directed to novel organophosphorus and organosulfur compounds, compositions comprising the compounds, and methods of using the compounds as cleaning agents, dispersants, surfactants, biofilm removal agents, and antibiofilm, antifouling, antimicrobial, and anti-fungal agents.

In one aspect, the invention is directed to compounds represented by Formula I, or a salt thereof, and methods of using the compounds as a cleaning agent, dispersant, surfactant, biofilm removal agent, antibiofilm, antifouling, antimicrobial, and/or anti-fungal agent:

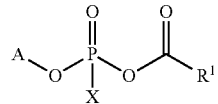

Formula I where A is $C_{1-10}$ hydrocarbyl or optionally $R^1$ substituted $C_{1-10}$ hydrocarbyl; X is —NHR, —NHOR, —NHCOR, —NHOCOR, or —OR; and R is H or $C_{1-10}$ hydrocarbyl; $R^1$ is selected from hydrogen, halogen, cyano, OH, $C_{1-6}$ hydrocarbyl, $C_{1-6}$ alkoxy, $SOR^2$, $SO_2R^2$, $SO_2NR^3R^4$ $COR^2$, $CO_2R^2$, $CONR^3R^4$, $NR^3R^4$, $NR^3COR^4$, $NR^3SO_2R^4$, $NR^3CO_2R^4$, $NR^3CONR^4$, $OCOR^2$, and phosphonic acid, wherein each of $C_{1-6}$ hydrocarbyl, $C_{1-6}$ alkoxy, $SOR^2$, $SO_2R^2$, $SO_2NR^3R^4$, $COR^2$, $CO_2R^2$, $CONR^3R^4$, $NR^3R^4$, $NR^3COR^4$, $NR^3SO_2R^4$, $NR^3CO_2R^4$, $NR^3CONR^4$, $OCOR^2$, can be optionally substituted with halo, amino, hydroxyl, $C_{1-6}$ hydrocarbyl, $C_{1-6}$ alkoxy, cyano, or phosphonic acid; $R^2$, $R^3$ and $R^4$ are independently selected from hydrogen, $C_{1-6}$ hydrocarbyl, in which each of the $C_{1-6}$ hydrocarbyl can be optionally substituted with halo, amino, hydroxyl, $C_{1-6}$ alkoxy, cyano, or phosphonic acid.

In one aspect, the invention is directed to compounds represented by Formula II, or a salt thereof, and methods of using the compounds as a cleaning agent, dispersant, surfactant, biofilm removal agent, antibiofilm, antifouling, antimicrobial, and/or anti-fungal agent:

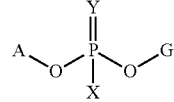

Formula II where A is R, Y is O or S, X is $NH_2$, OH, or OR, and G is R, where R is $C_{1-10}$ hydrocarbyl.

In one aspect, the invention is directed to a compound represented by Formula III, or a salt thereof, and methods of using the compound as a cleaning agent, dispersant, surfactant, biofilm removal agent, antibiofilm, antifouling, antimicrobial, and/or anti-fungal agent:

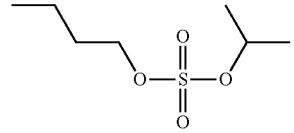

Formula III

The compounds of Formula I, Formula II, or Formula III, or compositions comprising compounds of Formula I, Formula II, or Formula III may be used for cleaning, decontaminating surfaces, dispersing surface particles, reducing or preventing fungal or microbial growth, such as growth of a bacteria or a biofilm, or for dispersing, removing or inhibiting biofilms, or as anti-fouling agents.

The methods of the present disclosure include methods of cleaning, decontaminating surfaces, dispersing surface particles, dispersing, removing or inhibiting the growth of a biofilm, or inhibiting the growth of, or killing a fungus or bacteria, comprising contacting the surface, biofilm, fungus or bacteria with an amount of a compound of Formula I, Formula II, or Formula III, or a composition comprising an amount of a compound of Formula I, Formula II, or Formula III, wherein the amount of the compound of Formula I, Formula II, or Formula III is effective to clean and decontaminate surfaces, disperse, remove or inhibit the growth of the biofilm, or inhibit the growth of, or kill the fungus or bacteria.

In some embodiments, the methods are methods of cleaning and decontaminating a surface, dispersing surface particles, dispersing, removing or inhibiting the growth of a biofilm comprising contacting the surface or biofilm with an amount of a compound of Formula I, Formula II, or Formula III, or a composition comprising an amount of a compound of Formula I, Formula II, or Formula III, wherein the amount of the compound of Formula I, Formula II, or Formula III is effective to clean or decontaminate a surface, disperse surface particles, disperse, remove, or inhibit the growth of the biofilm.

In some embodiments, the methods comprise contacting the surface with an amount of a compound of Formula I, Formula II, or Formula III effective to clean or decontaminate a surface or disperse surface particles.

In some embodiments, the methods comprise contacting the surface with a composition comprising an amount of a compound of Formula I, Formula II, or Formula III effective to clean or decontaminate a surface or disperse surface particles.

In some embodiments, the methods comprise contacting the biofilm with an amount of a compound of Formula I, Formula II, or Formula III effective to disperse, remove or inhibit the growth of the biofilm.

In some embodiments, the methods comprise contacting the biofilm with a composition comprising an amount of a compound of Formula I, Formula II, or Formula III effective to disperse, remove or inhibit the growth of the biofilm.

In some embodiments, the methods are methods of inhibiting the growth of, or killing a fungus or bacteria, comprising contacting the fungus or bacteria with an amount of a compound of Formula I, Formula II, or Formula III, or a composition comprising an amount of a compound of Formula I, Formula II, or Formula III, wherein the amount of the compound of Formula I Formula II, or Formula III is effective to inhibit the growth of or kill the fungus or bacteria.

In some embodiments, the methods comprise contacting the fungus or bacteria with an amount of a compound of Formula I, Formula II, or Formula III effective to inhibit the growth of or kill the fungus or bacteria.

In some embodiments, the methods comprise contacting the fungus or bacteria with a composition comprising an amount of a compound of Formula I, Formula II, or Formula III effective to inhibit the growth of or kill the fungus or bacteria.

Some embodiments include a method of reducing or preventing fungal or microbial growth on a surface comprising applying an effective amount of a compound of Formula I, Formula II, or Formula III, or a composition comprising a compound of Formula I, Formula II, or Formula III to a surface, such as a surface susceptible to contamination, fungal or microbial growth or biofilm formation.

In some embodiments, the surface is a living surface, such as human or animal tissue. In some embodiments, the surface is a non-living surface, such as indwelling medical devices, or surfaces exposed to water, such as industrial equipment and marine vessels.

DETAILED DESCRIPTION

Unless specifically defined herein, all terms used herein have the same meaning as they would to one skilled in the art of the present disclosure.

As used herein, the term "antimicrobial" refers to an agent that is effective against pathogenic microorganisms, including bacteria, fungi, viruses, protozoa, and biofilms. Antimicrobial agents can be used to disperse, remove, inhibit, reduce, or prevent microbial growth.

The term "heteroatom" refers to any atom other than carbon, for example, N, O, or S.

The term "substituents" refers to groups such as hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, aldehyde, acyl, oxyacyl, carboxyl, sulfonyl, sulfonamide, sulfuryl, and the like.

The term "hydrocarbyl" refers to univalent groups formed by removing a hydrogen atom from a hydrocarbon, e.g. alkyl, cycloalkyl, alkenyl, alkynyl, aryl, alkylaryl, arylalkyl, arylalkenyl, arylalkynyl, and arylene. The term "substituted hydrocarbyl" refers to hydrocarbyl groups further bearing one or more substituents as defined herein.

The term "alkyl" refers to a monovalent straight or branched chain hydrocarbon group having from one to about 12 carbon atoms, for example, methyl, ethyl, n-propyl, iso-propyl, n-butyl, iso-butyl, tert-butyl, n-pentyl (also known as n-amyl), n-hexyl, and the like. The term "substituted alkyl" refers to alkyl groups further bearing one or more substituents as defined herein.

The term "alkenyl" refers to straight-chained or branched hydrocarbyl groups having at least one carbon-carbon double bond, and having between about 2 and about 12 carbon atoms, and the term "substituted alkenyl" refers to alkenyl groups further bearing one or more substituents as defined herein.

The term "alkynyl" refers to straight-chained or branched hydrocarbyl groups having at least one carbon-carbon triple bond, and having between about 2 and about 12 carbon atoms, and the term "substituted alkynyl" refers to alkynyl groups further bearing one or more substituents as defined herein.

The term "alkoxy" refers to the moiety —O-alkyl, wherein alkyl is as defined above, and the term "substituted alkoxy" refers to alkoxy groups further bearing one or more substituents as defined herein.

The term "cycloalkyl" refers to alkyl groups having between 3 and about 8 carbon atoms arranged as a ring, and the term "substituted cycloalkyl" refers to cycloalkyl groups further bearing one or more substituents as defined herein.

The term "aromatic" refers to a cyclically conjugated molecular entity with a stability, due to delocalization, significantly greater than that of a hypothetical localized structure, such as the Kekule structure.

The term "heterocyclic," when used to describe an aromatic ring, refers to the aromatic rings containing at least one heteroatom, as defined above. The term "heterocyclic," when not used to describe an aromatic ring, refers to cyclic (i.e., ring-containing) groups other than aromatic groups, the cyclic group being formed by between 3 and about 14 carbon atoms and at least one heteroatom as defined herein.

The term "substituted heterocyclic" refers, for both aromatic and non-aromatic structures, to heterocyclic groups further bearing one or more substituents as defined herein.

The term "aryl" refers to aromatic groups having between about 5 and about 14 carbon atoms and the term "substituted aryl" refers to aryl groups further bearing one or more substituents as defined herein.

The term "heteroaryl" refers to aromatic rings, where the ring structure is formed by between 3 and about 14 carbon atoms and by at least one heteroatom described above, and the term "substituted heteroaryl" refers to heteroaryl groups further bearing one or more substituents as defined herein.

The term "alkylaryl" refers to alkyl-substituted aryl groups and the term "substituted alkylaryl" refers to alkylaryl groups further bearing one or more substituents as defined herein.

The term "arylalkyl" refers to aryl-substituted alkyl groups and the term "substituted arylalkyl" refers to arylalkyl groups further bearing one or more substituents as defined herein.

The term "arylalkenyl" refers to aryl-substituted alkenyl groups and the term "substituted arylalkenyl" refers to arylalkenyl groups further bearing one or more substituents as defined herein.

The term "arylalkynyl" refers to aryl-substituted alkynyl groups and the term "substituted arylalkynyl" refers to arylalkynyl groups further bearing one or more substituents as defined herein.

The term "arylene" refers to divalent aromatic groups having between 5 and about 14 carbon atoms and the term "substituted arylene" refers to arylene groups further bearing one or more substituents as defined herein.

The present disclosure is directed to organophosphorus or organosulfur compounds, compositions comprising one or more compounds, and methods of using the compounds or compositions as cleaning agents, dispersants, surfactants, biofilm removal agents, biofilm dispersants, removers, and antibiofilm, antifouling, antimicrobial, and anti-fungal agents.

In one aspect, the present disclosure is directed to compounds represented by Formula I:

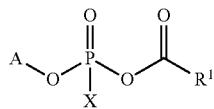

Formula I or a salt thereof; where A is $C_{1-10}$ hydrocarbyl or optionally $R^1$ substituted $C_{1-10}$ hydrocarbyl; X is —NHR, —NHOR, —NHCOR, —NHOCOR, or —OR; and R is H or $C_{1-10}$ hydrocarbyl;
$R^1$ is selected from hydrogen, halogen, cyano, OH, $C_{1-6}$ hydrocarbyl, $C_{1-6}$ alkoxy, $SOR^2$, $SO_2R^2$, $SO_2NR^3R^4$ $COR^2$, $CO_2R^2$, $CONR^3R^4$, $NR^3R^4$, $NR^3COR^4$, $NR^3SO_2R^4$, $NR^3CO_2R^4$, $NR^3CONR^4$, $OCOR^2$, and phosphonic acid, wherein each of $C_{1-6}$ hydrocarbyl, $C_{1-6}$ alkoxy, $SOR^2$, $SO_2R^2$, $SO_2NR^3R^4$, $COR^2$, $CO_2R^2$, $CONR^3R^4$, $NR^3R^4$, $NR^3COR^4$, $NR^3SO_2R^4$, $NR^3CO_2R^4$, $NR^3CONR^4$, $OCOR^2$, can be optionally substituted with halo, amino, hydroxyl, $C_{1-6}$ hydrocarbyl, $C_{1-6}$ alkoxy, cyano, or phosphonic acid; $R^2$, $R^3$ and $R^4$ are independently selected from hydrogen, $C_{1-6}$ hydrocarbyl, in which each of the $C_{1-6}$ hydrocarbyl can be optionally substituted with halo, amino, hydroxyl, $C_{1-6}$ alkoxy, cyano, or phosphonic acid.

With respect to any relevant structural representation, such as Formula I, X is —NHR, —NHCOR, —NHOR, —NHOCOR, or —OR. In some embodiments, X is —NHR. In some embodiments, X is —NH$_2$. In some embodiments, X is OH. In some embodiments, X is OR.

With respect to any relevant structural representation, such as Formula I, R is H or $C_{1-10}$ hydrocarbyl, including $C_{1-10}$ alkyl (e.g. methyl; $C_2$ alkyl, such as ethyl; $C_3$ alkyl, such as propyl, isopropyl, cyclopropyl, etc.; $C_4$ alkyl, such as linear, branched or cyclic, butyl, etc.; $C_5$ alkyl, $C_6$ alkyl, $C_7$ alkyl, $C_8$ alkyl, $C_9$ alkyl, or $C_{10}$ alkyl), $C_{1-6}$ alkyl, $C_{1-3}$ alkyl, $C_{1-10}$ alkenyl (e.g. $C_2$ alkenyl, such as vinyl; $C_3$ alkenyl, such as —CH$_2$—CH=CH$_2$, $C_4$ alkenyl, such as linear, branched or cyclic, butenyl, etc.; $C_5$ alkenyl, $C_6$ alkenyl, $C_7$ alkenyl, $C_8$ alkenyl, $C_9$ alkenyl, or $C_{10}$ alkenyl), $C_{2-6}$ alkenyl, $C_{2-4}$ alkenyl, optionally substituted aryl, such as phenyl or hydrocarbyl substituted phenyl, naphthyl, etc. In some embodiments, R is H. In some embodiments, R is $C_{1-6}$ alkyl. In some embodiments, R is $C_{1-3}$ alkyl. In some embodiments, R is CH$_3$.

With respect to any relevant structural representation, such as Formula I, A is $C_{1-10}$ hydrocarbyl, including $C_{1-10}$ alkyl (e.g. methyl; $C_2$ alkyl, such as ethyl; $C_3$ alkyl, such as propyl, isopropyl, cyclopropyl, etc.; $C_4$ alkyl, such as linear, branched or cyclic, butyl, etc.; $C_5$ alkyl, $C_6$ alkyl, $C_7$ alkyl, $C_8$ alkyl, $C_9$ alkyl, or $C_{10}$ alkyl), $C_{1-6}$ alkyl, $C_{1-3}$ alkyl, $C_{1-10}$ alkenyl (e.g. $C_2$ alkenyl, such as vinyl; $C_3$ alkenyl, such as —CH$_2$—CH=CH$_2$, $C_4$ alkenyl, such as linear, branched or cyclic, butenyl, etc.; $C_5$ alkenyl (such as isopentenyl), $C_6$ alkenyl, $C_7$ alkenyl, $C_8$ alkenyl, $C_9$ alkenyl, or $C_{10}$ alkenyl), $C_{2-6}$ alkenyl, $C_{2-4}$ alkenyl, optionally substituted aryl, such as phenyl or hydrocarbyl substituted phenyl, naphthyl, etc.

With respect to any relevant structural representation, such as Formula I, in some embodiments, A is $C_{3-6}$ alkyl. In some embodiments, A is $C_3$ alkyl, such as n-propyl, isopropyl, or cyclopropyl. In some embodiments, A is n-propyl. In some embodiments, A is isopropyl. In some embodiments, A is $C_4$ alkyl, such as n-butyl, t-butyl, or cyclobutyl. In some embodiments, A is n-butyl. In some embodiments, A is t-butyl. In some embodiments, A is $C_5$ alky, such as n-pentyl, isopentyl, cyclopentyl, etc. In some embodiments, A is n-pentyl. In some embodiments, A is isopentyl. In some embodiments, A is $C_6$ alkyl, such as n-hexyl, cyclohexyl, etc. In some embodiments, A is n-hexyl. In some embodiments, A is $C_{3-5}$ alkenyl, such as propenyl, butenyl, isopentenyl, pentenyl, etc. In some embodiments, A is $C_5$ alkenyl. In some embodiments, A is isopentenyl. In Some embodiments, A is prenyl.

With respect to any relevant structural representation, such as Formula I, in some embodiments, A is —(CH$_2$)$_{1-2}$-Cy, wherein Cy is optionally substituted cycloalkyl (such as cyclopropyl, cyclobutyl, cyclopentyl, cyclohexyl) or optionally substituted phenyl. In some embodiments, A is

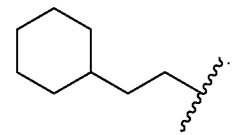 [SMILES: *CCC1CCCCC1]

In some embodiments, A is

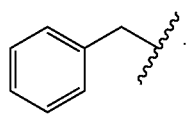 [SMILES: *Cc1ccccc1]

In one aspect, the present disclosure is directed to methods of using a compound of Formula I as a cleaning agent, dispersant, surfactant, biofilm removal agent, biofilm dispersant, antibiofilm, antifouling, antimicrobial, and/or antifungal agent.

In some embodiments of Formula I, X is $NH_2$. Compounds of Formula I where X is $NH_2$, and the compounds have dispersant, antibiofilm, antifouling, antifungal, and/or antimicrobial activity, include compounds having the following structures as shown in Table 1.

TABLE 1

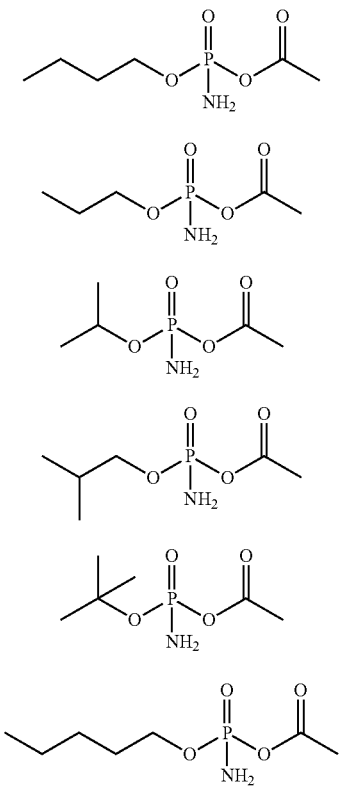

Compounds of Formula I where X is $NH_2$, and the compounds may have dispersant, antibiofilm, antifouling, antifungal, and/or antimicrobial activity, include compounds having the following structures as shown in Table 2.

TABLE 2

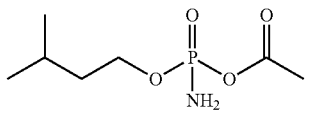

TABLE 2-continued

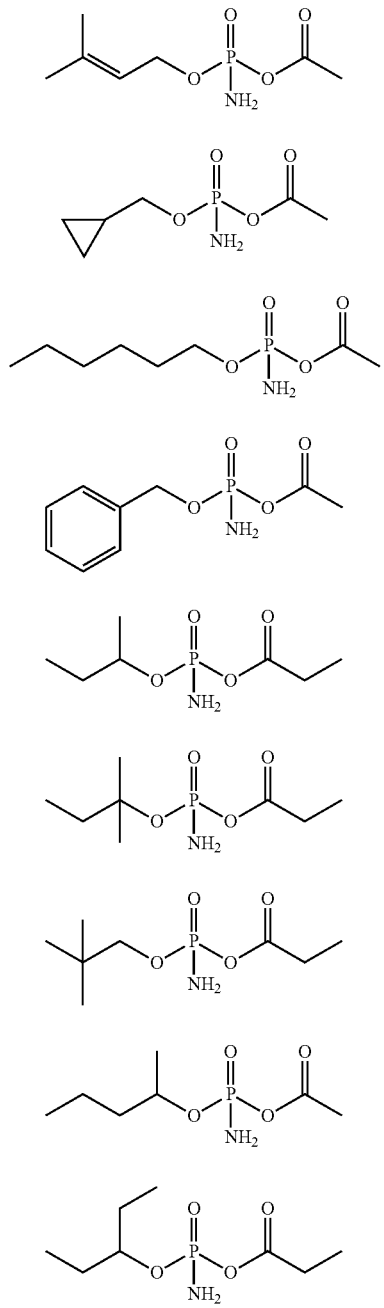

In some embodiments of Formula I, X is OH. Compounds of Formula I where X is OH, and the compounds have dispersant, antibiofilm, antifouling, antifungal, and/or antimicrobial activity, include compounds having the following structures as shown in Table 3.

TABLE 3

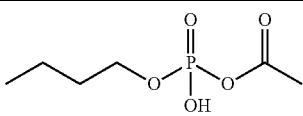

TABLE 3-continued
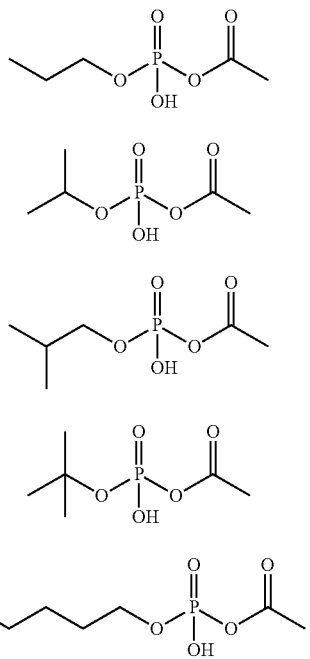
In some embodiments of Formula I, X is OR. Compounds of Formula I where X is OR, and R is hydrocarbyl, and the compounds may have dispersant, antibiofilm, antifouling, antifungal, and/or antimicrobial activity include compounds having the following structures as shown in Table 4.
TABLE 4
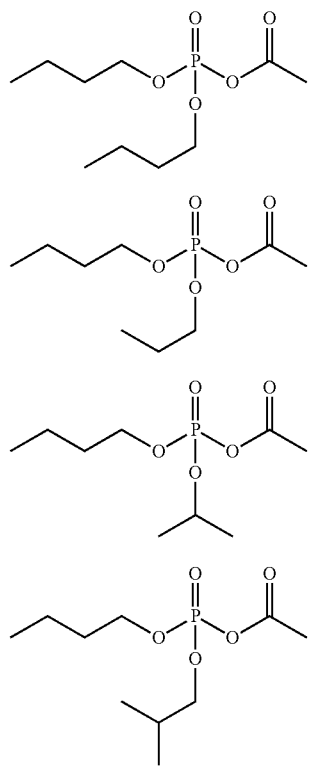
TABLE 4-continued
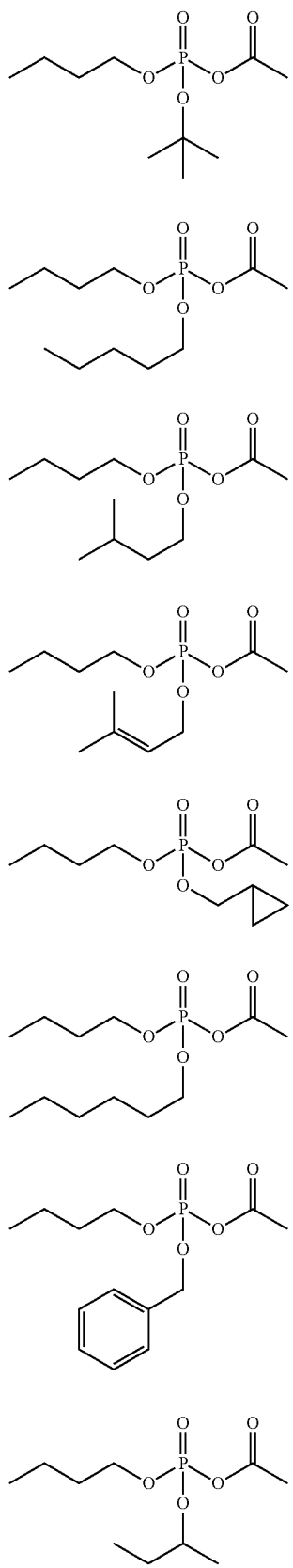

TABLE 4-continued

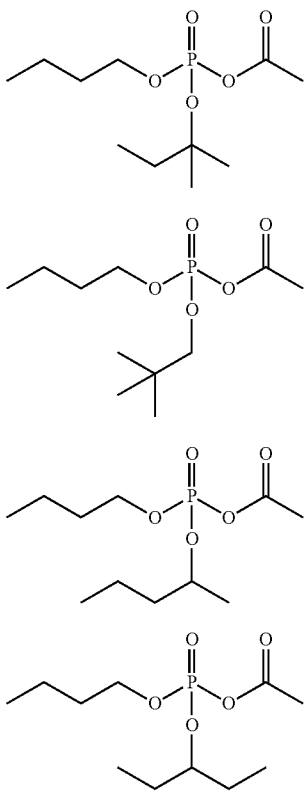

In one aspect, the present disclosure is directed to compounds represented by Formula II:

Formula II

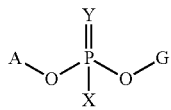

or a salt thereof, where A is R, Y is O or S, X is $NH_2$, OH, or OR, and G is H or R, where R is $C_{1-10}$ hydrocarbyl.

In some embodiments of Formula II, X is $NH_2$, A is $(CH_2)_3CH_3$, Y is O, and G is OR, where R is $C_{1-10}$ hydrocarbyl.

In one aspect, the present disclosure is directed to methods of using a compound of Formula II as a cleaning agent, dispersant, surfactant, biofilm removal agent, biofilm dispersant, antibiofilm, antifouling, antimicrobial, and/or antifungal agent.

One embodiment of Formula II, where X is $NH_2$, A is $(CH_2)_3CH_3$, Y is O, and G is OR, where R is $C_5H_9$, that has cleaning, dispersant, surfactant, biofilm dispersant, antibiofilm, antifouling, antifungal, and/or antimicrobial activity is represented by the following structure:

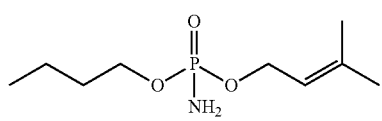

Compounds of Formula II where X is $NH_2$, A is $(CH_2)_3CH_3$, Y is O, and G is OR, where R is $C_{1-10}$ hydrocarbyl, that may have dispersant, antibiofilm, antifouling, antifungal, and/or antimicrobial activity include compounds having the following structures as shown in Table 5.

TABLE 5

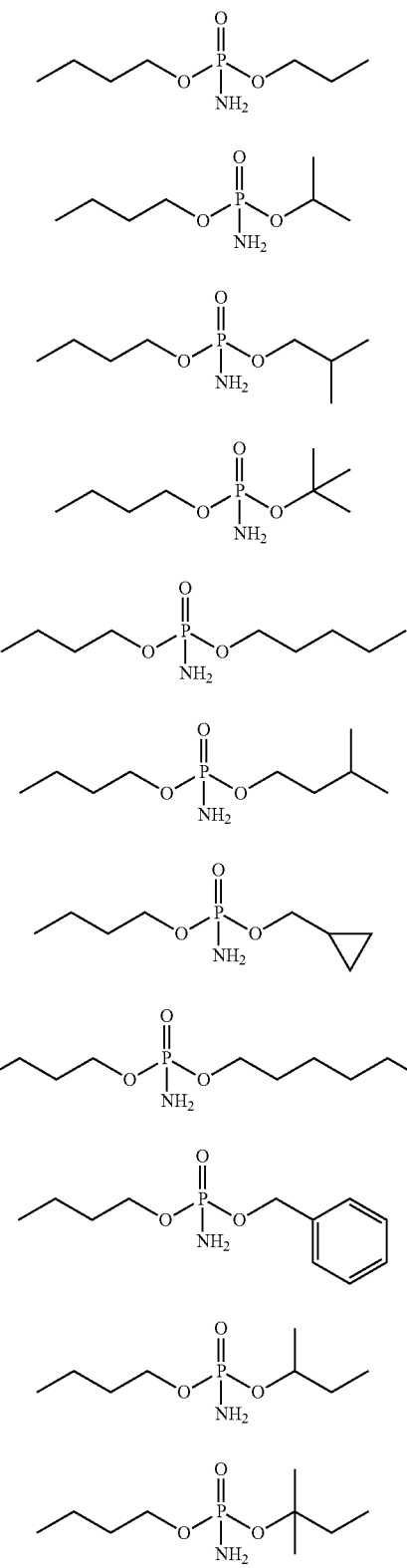

TABLE 5-continued

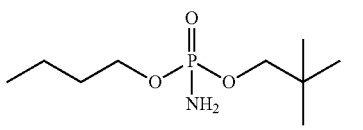

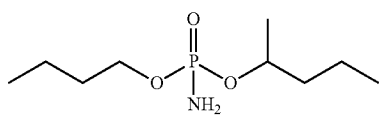

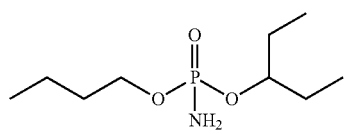

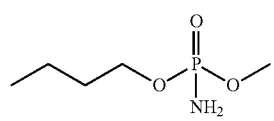

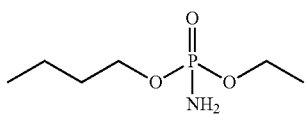

In some embodiments of Formula II, X is OH, A is R, Y is O, and G is OR, where R is $C_{1-10}$ hydrocarbyl.

One embodiment of Formula II, where X is OH, A is R, Y is O, and G is OR, that has cleaning, dispersant, surfactant, biofilm dispersant, removal, antibiofilm, antifouling, antifungal, and/or antimicrobial is represented by the following structure:

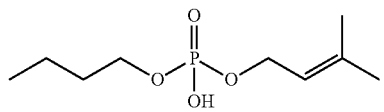

One embodiment of Formula II, where X is $NH_2$, Y is S, A is $(CH_2)_3CH_3$, and G is $CH(CH_3)_2$, that may have cleaning, dispersant, surfactant, antibiofilm, antifouling, antifungal, and/or antimicrobial activity, is represented by the following structure:

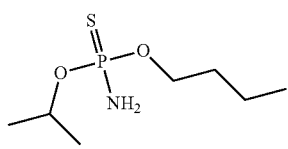

In one aspect the present disclosure is directed to a compound represented by Formula III:

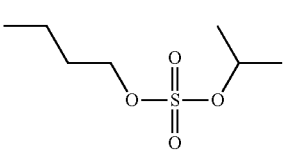

Formula III

In one aspect the present disclosure is directed to methods of using the compound of Formula III as a cleaning agent, dispersant, surfactant, biofilm removal agent, biofilm dispersant, antibiofilm, antifouling, antimicrobial, and/or antifungal agent.

In one aspect of the present disclosure, the compounds of Formula I, Formula II, or Formula III ("subject compound") may be used to clean or decontaminate a surface, disperse surface particles, or disperse, inhibit, reduce, or prevent fungal or microbial growth. For example, a subject compound may be used to reduce or prevent microbial formation of a biofilm. A biofilm includes an assemblage of surface-associated microbial cells that forms on an extracellular surface.

In one embodiment, the methods of the present disclosure are methods of dispersing, removing or inhibiting the growth of a biofilm, or inhibiting the growth of, or killing a fungus or bacteria, comprising contacting the biofilm, fungus or bacteria with an amount of a compound of Formula I, or a composition comprising an amount of a compound of Formula I, wherein the amount of the compound of Formula I is effective to disperse or inhibit the growth of the biofilm, or inhibit the growth of, or kill the fungus or bacteria.

In some embodiments, the methods are methods of dispersing, removing or inhibiting the growth of a biofilm comprising contacting the biofilm with an amount of a compound of Formula I, or a composition comprising an amount of a compound of Formula I, wherein the amount of the compound of Formula I is effective to disperse or inhibit the growth of the biofilm.

In some embodiments, the methods comprise contacting the biofilm with an amount of a compound of Formula I effective to disperse or inhibit the growth of the biofilm.

In some embodiments, the methods comprise contacting the biofilm with a composition comprising an amount of a compound of Formula I effective to disperse or inhibit the growth of the biofilm.

In some embodiments, the methods are methods of inhibiting the growth of, or killing a fungus or bacteria, comprising contacting the fungus or bacteria with an amount of a compound of Formula I, or a composition comprising an amount of a compound of Formula I, wherein the amount of the compound of Formula I is effective to inhibit the growth of or kill the fungus or bacteria.

In some embodiments, the methods comprise contacting the fungus or bacteria with an amount of a compound of Formula I effective to inhibit the growth of or kill the fungus or bacteria.

In some embodiments, the methods comprise contacting the fungus or bacteria with a composition comprising an amount of a compound of Formula I effective to inhibit the growth of or kill the fungus or bacteria.

In one embodiment, the methods of the present disclosure are methods of dispersing, removing or inhibiting the growth of a biofilm, or inhibiting the growth of, or killing a fungus or bacteria, comprising contacting the biofilm, fungus or bacteria with an amount of a compound of Formula II, or a composition comprising an amount of a compound of Formula II, wherein the amount of the compound of Formula II is effective to disperse or inhibit the growth of the biofilm, or inhibit the growth of, or kill the fungus or bacteria.

In some embodiments, the methods are methods of dispersing, removing, or inhibiting the growth of a biofilm comprising contacting the biofilm with an amount of a compound of Formula II, or a composition comprising an amount of a compound of Formula II, wherein the amount of the compound of Formula II is effective to disperse or inhibit the growth of the biofilm.

In some embodiments, the methods comprise contacting the biofilm with an amount of a compound of Formula II effective to disperse or inhibit the growth of the biofilm.

In some embodiments, the methods comprise contacting the biofilm with a composition comprising an amount of a compound of Formula II effective to disperse or inhibit the growth of the biofilm.

In some embodiments, the methods are methods of inhibiting the growth of, or killing a fungus or bacteria, comprising contacting the fungus or bacteria with an amount of a compound of Formula II, or a composition comprising an amount of a compound of Formula II, wherein the amount of the compound of Formula II is effective to inhibit the growth of or kill the fungus or bacteria.

In some embodiments, the methods comprise contacting the fungus or bacteria with an amount of a compound of Formula II effective to inhibit the growth of or kill the fungus or bacteria.

In some embodiments, the methods comprise contacting the fungus or bacteria with a composition comprising an amount of a compound of Formula II effective to inhibit the growth of or kill the fungus or bacteria.

In one embodiment, the methods of the present disclosure are methods of dispersing, removing or inhibiting the growth of a biofilm, or inhibiting the growth of, or killing a fungus or bacteria, comprising contacting the biofilm, fungus or bacteria with an amount of a compound of Formula III, or a composition comprising an amount of a compound of Formula III, wherein the amount of the compound of Formula III is effective to disperse or inhibit the growth of the biofilm, or inhibit the growth of, or kill the fungus or bacteria.

In some embodiments, the methods are methods of dispersing, removing or inhibiting the growth of a biofilm comprising contacting the biofilm with an amount of a compound of Formula III, or a composition comprising an amount of a compound of Formula III, wherein the amount of the compound of Formula III is effective to disperse or inhibit the growth of the biofilm.

In some embodiments, the methods comprise contacting the biofilm with an amount of a compound of Formula III effective to disperse or inhibit the growth of the biofilm.

In some embodiments, the methods comprise contacting the biofilm with a composition comprising an amount of a compound of Formula III effective to disperse or inhibit the growth of the biofilm.

In some embodiments, the methods are methods of inhibiting the growth of, or killing a fungus or bacteria, comprising contacting the fungus or bacteria with an amount of a compound of Formula III, or a composition comprising an amount of a compound of Formula III, wherein the amount of the compound of Formula III is effective to inhibit the growth of or kill the fungus or bacteria.

In some embodiments, the methods comprise contacting the fungus or bacteria with an amount of a compound of Formula III effective to inhibit the growth of or kill the fungus or bacteria.

In some embodiments, the methods comprise contacting the fungus or bacteria with a composition comprising an amount of a compound of Formula III effective to inhibit the growth of or kill the fungus or bacteria.

In one embodiment, a compound of Formula I, Formula II, or Formula III is present in a composition at a concentration of from about 0.001 to about 10% by weight, based on 100% total weight of the composition and more preferably from about 0.1 to about 1 or 2% by weight, based on 100% total weight of the composition.

According to another embodiment, the compound is present at a concentration of from about 10-30% by weight, based on 100% total weight of the composition.

According to another embodiment, the compound is present at a concentration of from about 5-85% by weight, based on 100% total weight of the composition.

Generally, the compounds of the present invention reduce the number of microorganisms (bacteria, fungi, and/or algae) by 95, 99, 99.9, or 99.99% typically within an hour and maintains efficacy over long periods of time.

The compounds of the present invention prevent and/or remove bacterial, fungal, and/or algae biofilm by 95, 99, 99.9, or 99.99% typically within 10 minutes and maintains efficacy over long periods of time.

The compounds of the present invention disperse particles by 45-100% within 30 minutes, dependent on the size of the particle, and maintains efficacy over long periods of time.

Biofilms may form on a wide variety of surfaces, including living tissues, indwelling medical devices, industrial or potable water system piping, or natural aquatic systems. Subject compounds can be used as cleaning agents, emulsifiers, dispersants, surfactants, or antifungal, antibiofilm, antifouling, antibacterial or bactericidal agents to remove disease-causing organisms from external surfaces, including human and animal tissue such as skin and wounds. They can be used in different products such as soaps, detergents, deodorizers, stain removers, health and skincare products, cosmetics, antiseptics, and household, industrial, institutional, and clinical cleaners. They can also be used to remove algae, mold, or slime. Subject compounds can be used alone, or in combination with other antimicrobial or antifungal agents.

A spectrum of indwelling medical devices (e.g., ocular lenses, dental implants, central venous catheters and needleless connectors, endotracheal tubes, intrauterine devices, mechanical heart valves, coronary stents, vascular bypass grafts, pacemakers, peritoneal dialysis catheters, prosthetic joints, central nervous system shunts, tympanostomy tubes, urinary catheters, and voice prostheses) or other devices used in the health-care environment have been shown to harbor biofilms, resulting in measurable rates of device-associated infections.

The subject compounds can be used on the surface of or within medical devices to provide long term protection against bacterial colonization and reduce the incidence of device-related infections. These substances can also be incorporated as an anti-biofilm forming agent, in combination with an antibiotic, into coatings for indwelling medical devices, instruments, and other clinical surfaces. Coatings will sufficiently kill or inhibit the initial colonizing bacteria and prevent device-related infection as long as the substance is presented in an inhibitory concentration at the device-microbe interface.

The subject compounds, either administered alone or as part of a coating or medical device, can reduce or prevent biofilms. In certain embodiments, biofilms are reduced by about 1.0 log, about 1.5 logs, about 2.0 logs, about 2.5 logs, about 3.0 logs, about 3.5 logs, about 4.0 logs, about 4.5 logs, or about 5.0 logs, or by any number bound by the range of about 1.0 to about 5.0 logs.

The medical devices which are amenable to coatings of the subject anti-biofilm substances generally have surfaces composed of thermoplastic or polymeric materials such as polyethylene, Dacron, nylon, polyesters, polytetrafluoroethylene, polyurethane, latex, silicone elastomers and the like. Devices with metallic surfaces are also amenable to coatings with the anti-biofilm substances. Such devices, for example bone and joint prosthesis, can be coated by cement mixture containing the subject anti-biofilm substances. During implant use, the anti-biofilm substances leach from the cement into the surrounding prosthesis surface environment.

Various methods can be employed to coat the surfaces of medical devices with the anti-biofilm substances. For example, one of the simplest methods would be to flush the surfaces of the device with a solution of the anti-biofilm substance. The flushing solution would normally be composed of sterile water or sterile normal saline solutions. Another method of coating the devices would be to first apply or adsorb to the surface of the medical device a layer of tridodecylmethyl ammonium chloride (TDMAC) surfactant followed by a coating layer of anti-biofilm substance. For example, a medical device having a polymeric surface, such as polyethylene, silastic elastomers, polytetrafluoroethylene or Darcon, can be soaked in a 5% by weight solution of TDMAC for 30 minutes at room temperature, air dried, and rinsed in water to remove excess TDMAC. Alternatively, TDMAC precoated catheters are commercially available; for example, arterial catheters coated with TDMAC are available from Cook Critical Care, Bloomington, Ind. The device carrying the absorbed TDMAC surfactant coated can then be incubated in a solution of the anti-biofilm substance for one hour or so, washed in sterile water to remove unbound anti-biofilm substance and stored in a sterile package until ready for implantation. A further method useful to coat the surface of medical devices with the subject antibiotic combinations involves first coating the selected surfaces with benzalkonium chloride followed by ionic bonding of the anti-biofilm substance composition. Alternative methods and reagents provided in U.S. Pat. Nos. 4,107,121, 4,442,133, 4,678,660 and 4,749,585, 4,895,566, 4,917,686, 4,952,419, and 5,013, 30, can be used to coat devices with the anti-biofilm substances disclosed herein.

A subject compound can be directly incorporated into the polymeric matrix of the medical device at the polymer synthesis stage or at the device manufacture stage. A subject compound can also be covalently attached to the medical device polymer.

Biofilms in industrial systems cause severe clogging, contamination, corrosion, scale, slime, and biodeterioration. Bacterial contamination of the water distribution systems can occur if biofilms are sloughed off naturally or removed by treatment. Biofilms in drinking water piping systems accommodate *Escherichia coli, Helicobacter pylori, Mycobacterium* spp., and protozoa infected with *Legionella pneumophila*. This results in decreased water quality and increased treatment costs and health risks. Biofilms in pipes, fixtures and containers carrying water or other liquids cause reduced flow and increased resistance to flow. Formation of biofilms on probes, sensors, screens and filters results in reduced efficiency. Microbial films that grow on the walls of heat exchanger tubes create additional heat transfer and fluid flow resistances. Formation of biofilms on ship hulls leads to biofouling resulting in increased fuel consumption and cleaning costs. The food industry is also affected by the contamination caused by these films which adhere easily to the walls of food processing equipment, and on the surface of food itself. Biofilms in cooling towers results in reduced performance, degradation of material and also provides a reservoir for pathogens. Building materials such as stone, bricks and concrete or clay based roof tiles, mortars and especially all new materials for insulation and damming of humidity often contain organic compounds and are very susceptible to growth of sub-aerial biofilms creating an anaesthetic biopatina and reducing durability. Chemical and physical biodeteriorative forces, phenomena and processes further create damage on old and new buildings. Depending on the environmental conditions water retention and penetration the surface biofilms may transform into networks going deeper into the material. Biocide impregnation of new materials and biocide treatments of monuments create health and environmental hazards. Biofilm on surfaces also captures pollutants, noxious particles, elements, spores, and other contaminants.

Subject compounds can be used as antibiofilm agents in industrial systems.

Fouling is an undesirable growth of biological material on a surface immersed in water. Fouling usually starts with adhering and spreading of populations of bacteria over surfaces that are in contact with water. The bacteria pioneers are followed by numerous different algae, invertebrate larvae, hydroids, bryozoans, sponges, tunicates, echinoderms, cnidarians, and coelenterates.

Marine fouling occurs not only on marine vessels such as ships' hulls and drive systems, but also on other structures exposed to water. Such structures may include: pilings, marine markers, undersea conveyances like cabling and pipes, fishing nets, bulkheads, cooling towers, and any device or structure that operates submerged.

A subject compound can be incorporated into marine coatings to limit undesirable marine fouling. The anti-fouling coatings of this disclosure offer significant advantages over previous attempts to solve marine fouling problems. The coatings disclosed herein can be formulated so as not to contain toxic materials (such as heavy metals), and still retain their efficacy. This avoids the environmental concerns associated with the use of heavy metal biocides.

In certain embodiments, a subject compound is incorporated into an anti-fouling paint. Anti-fouling paints comprising a subject compound may further contain binders(s), pigment(s), solvent(s) and additive(s). Solvents can carry the solid components of paint and may be used to obtain the desired viscosity and correct consistency. Examples of the solvent include, but not limited to, aromatic hydrocarbons such as xylene and toluene; aliphatic hydrocarbons such as hexane and heptane, esters such as ethyl acetate and butyl acetate; amides such as N-methylpyrrolidone and N,N-dimethylformamide; alcohols such as isopropyl alcohol and butyl alcohol; ethers such as dioxane, THF and diethyl ether; and ketones such as methyl ethyl ketone, methyl isobutyl ketone and methyl isoamyl ketone. The solvent may be used alone or in combination thereof.

The binder or resin is the basic solid film former that remains after the solvent has evaporated and may bind the pigment particles together into a cohesive paint film. The binder determines many of the necessary film properties such as adhesion, gloss level, hardness, abrasion resistance, flexibility, speed of drying and durability. Examples of binders include, but not limited to, alkyd resin, acrylic or vinyl emulsions, polyurethane resins, epoxy resins, silicone based resins, acrylic resins and inorganic silicate based resins. Among the binders which have been used in anti-fouling coatings are vinyl resins, particularly a vinyl chloride/vinyl acetate copolymer, and rosin.

The paint composition can contain one or more pigments. The pigments used in paint may be present as fine solid particles that are dispersed, but not soluble, in the binder and solvent. Examples of pigments include, but are not limited to, titanium dioxide, cuprous oxide, iron oxide, talc, aluminum flakes, mica flakes, ferric oxide, cuprous thiocyanate, zinc oxide, cupric acetate meta-arsenate, zinc chromate, zinc dimethyl dithiocarbamate, zinc ethylene bis(dithiocarbamate) and zinc diethyl dithiocarbamate.

Additive ingredients may optionally be incorporated into a coating composition. Examples of the additive ingredients are dehumidifiers, wetting/dispersing agents, surfactants, anti-settling agents, anti-skinning agents, drying/curing agents, anti-marring agents and additives ordinarily employed in coating compositions as stabilizers and anti-foaming agents. Also, any antibiotic which is toxic to gram negative organisms and which is relatively insoluble in seawater can be used with an anti-fouling marine paint.

The anti-fouling coatings so produced can be used for the submersible surfaces of boat hulls, pilings, buoys, floating or emplaced offshore platforms, submergence vehicles, navigational aids, ballast and other storage tanks, aquaculture netting, gear, and equipment, energy technologies, including current, wave, tidal, and other water hydrodynamic technologies, thermal energy technologies, water intake pipes, open an closed water systems, including for irrigation, cooling towers, pumps, reverse osmosis filters and membranes, and any structures or surfaces in contact with fresh or salt water where biofouling maybe a problem.

A subject compound may be used as an emulsifier, dispersant, surfactant, or cleaning agent.

In some embodiments, the methods of the present disclosure comprise applying to a surface a composition comprising an amount of a compound of Formula I effective to inhibit the growth of a biofilm on the surface. In some embodiments, the surface is an indwelling medical device. In some embodiments, the surface is a surface exposed to water. In some embodiments, the surface is a piece of industrial equipment. In some embodiments the surface is a marine vessel.

In some embodiments, the methods of the present disclosure comprise applying to a surface a composition comprising an amount of a compound of Formula I effective to inhibit the growth of a biofilm on the surface, wherein the composition is an anti-fouling paint or coating. In some embodiments, the anti-fouling paint or coating composition further comprises a binder, a pigment, a solvent, or an additive.

In some embodiments, the methods of the present disclosure comprise applying to a surface a composition comprising an amount of a compound of Formula I effective to inhibit the growth of a bacteria or a biofilm on the surface, wherein the composition is an antibacterial soap, an antibacterial detergent, an antibacterial health and skincare product, or an antibacterial household cleaning product.

In some embodiments, the methods of the present disclosure comprise applying to a surface a composition comprising an amount of a compound of Formula II effective to inhibit the growth of a biofilm on the surface. In some embodiments, the surface is an indwelling medical device. In some embodiments, the surface is a surface exposed to water. In some embodiments, the surface is a piece of industrial equipment. In some embodiments the surface is a marine vessel.

In some embodiments, the methods of the present disclosure comprise applying to a surface a composition comprising an amount of a compound of Formula II effective to inhibit the growth of a biofilm on the surface, wherein the composition is an anti-fouling paint or coating. In some embodiments, the anti-fouling paint or coating composition further comprises a binder, a pigment, a solvent, or an additive.

In some embodiments, the methods of the present disclosure comprise applying to a surface a composition comprising an amount of a compound of Formula II effective to inhibit the growth of a bacteria or a biofilm on the surface, wherein the composition is an antibacterial soap, an antibacterial detergent, an antibacterial health and skincare product, or an antibacterial household cleaning product.

In some embodiments, the methods of the present disclosure comprise applying to a surface a composition comprising an amount of a compound of Formula III effective to inhibit the growth of a biofilm on the surface. In some embodiments, the surface is an indwelling medical device. In some embodiments, the surface is a surface exposed to water. In some embodiments, the surface is a piece of industrial equipment. In some embodiments the surface is a marine vessel.

In some embodiments, the methods of the present disclosure comprise applying to a surface a composition comprising an amount of a compound of Formula III effective to inhibit the growth of a biofilm on the surface, wherein the composition is an anti-fouling paint or coating. In some embodiments, the anti-fouling paint or coating composition further comprises a binder, a pigment, a solvent, or an additive.

In some embodiments, the methods of the present disclosure comprise applying to a surface a composition comprising an amount of a compound of Formula III effective to inhibit the growth of a bacteria or a biofilm on the surface, wherein the composition is an antibacterial soap, an antibacterial detergent, an antibacterial health and skincare product, or an antibacterial household cleaning product.

EXAMPLES

Example 1

Synthesis of Embodiment of Formula I

Compounds of general Formula I, where X is $NH_2$, may be prepared according to the procedure shown in Scheme 1, using the applicable R—OH as a starting compound. In the pathway described below, the starting compound is n-butanol.

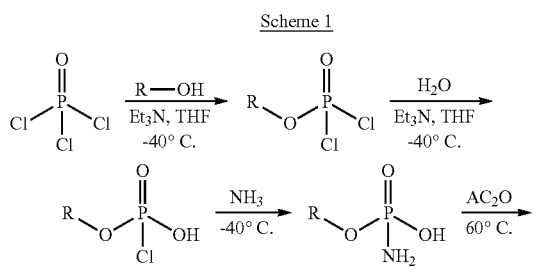

Scheme 1

-continued

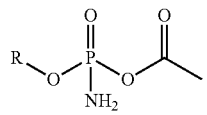

R = n-Butyl, n-propyl, isopropyl, iso-butyl, tert-butyl, n-pentyl

A solution of triethylamine (3.62 g, 36 mmol) and n-butanol (2.41 g, 32.6 mmol) in dry tetrahydrofuran (THF) (25 ml) was stirred at ambient temperature for 15-20 minutes under nitrogen atmosphere. The solution was added to a pre cooled solution of dry THF (35 mL) and POCl$_3$ (5 g, 32.6 mmol) at −40° C. over a period of 45 minutes under nitrogen atmosphere. The reaction mixture was stirred for 1 hour at −40° C. Progress of the reaction was monitored by GC-MS (Sample preparation: 0.25 mL of reaction mass was added to 0.5 mL of cold methanol and mixed well). Reaction mixture was filtered under nitrogen atmosphere and the solid cake (triethylamine hydrochloride salt) was washed with cold dry THF (10 mL). The filtrate was cooled to −40° C. in a round bottom flask, followed by the addition of triethylamine (3.62 g, 33 mmol), mixture of water (0.58 g, 32 mmol) and THF (0.6 mL) at −40° C. under nitrogen atmosphere. The reaction mixture was stirred for 1 hour at −40° C. and progress of the reaction was monitored by LC-MS. Reaction mixture was filtered under nitrogen atmosphere and solid cake was washed with cold THF (10 mL). The filtrate was cooled to −40° C. in a round bottom flask and purged (bubbled) ammonia gas to the reaction mixture for about 5 minutes (Observation: Exotherm 5° C.). Reaction mixture was stirred for 30 minutes at −40° C. and slowly raised the reaction mass temperature to ambient temperature with adequate venting and scrubbing of ammonia. Reaction mixture was stirred at ambient temperature for 1 hour and progress of the reaction was monitored by LC-MS. Acetic anhydride (4.99 g, 48.9 mmol) was added to the reaction mixture at 0° C. and raised the reaction mixture temperature gradually to 60° C. Reaction mixture stirred for 8 hour at 60° C. and monitored by LCMS. Reaction mixture was cooled to 25° C., filtered under nitrogen atmosphere and solid cake was washed with THF (10 mL). The combined filtrate was evaporated under reduced pressure at 30° C. to afford 3.8 g of acetic (1-butyl phosphoramidic) anhydride as off-white oily liquid with 61% yield (not corrected for purity). The crude product was further purified by preparative HPLC.

$^1$H NMR (400 MHz, CDCl$_3$) δ 0.90 (t, J=7.2 Hz, 3H), 1.35-1.45 (m, 2H merged with triethyl amine hydrochloride peaks), 1.55-1.70 (m, 2H), 2.03 (s, 3H), 3.80-4.00 (m, 2H), 4.18 (bs, 2H, NH$_2$); $^{31}$P (160 MHz, CDCl$_3$) δ 1.40; LC-MS (M+H) 196.2, (M−H) 193.8 at 0.8 minutes.

Example 2

Synthesis of Embodiment of Formula I

Compounds of general Formula I, where X is OH, may be prepared according to the procedure shown in Scheme 2, using the applicable R—OH as a starting compound. In the pathway shown below, the starting compound is n-butanol.

Scheme 2

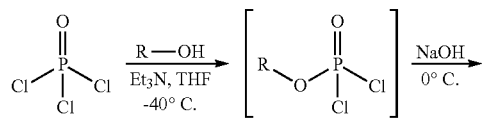

-continued

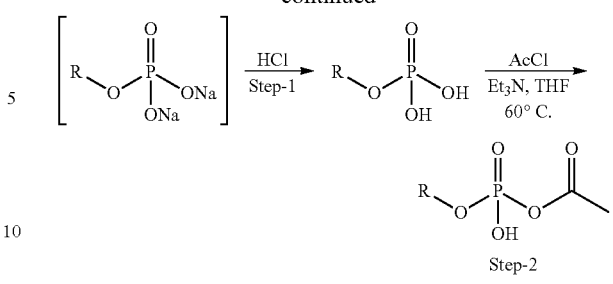

R = n-Butyl; —CH$_2$CH$_2$CH$_2$CH$_3$

Step 1: A solution of triethyl amine (4.99 g, 35.87 mmol) and n-butanol (2.41 g, 32.61 mmol) in dry tetrahydrofuran (THF) (25 ml) was stirred at ambient temperature for 15-20 minutes under nitrogen atmosphere. The solution was added to a pre cooled solution of dry THF (35 mL) and POCl$_3$ (5 g, 32.6 mmol) at −40° C. over a period of 20 minutes under nitrogen atmosphere. The reaction mixture was stirred for 2 hour at −40° C. The reaction mixture was filtered under nitrogen atmosphere and the solid cake (triethyl amine hydrochloride salt) was washed with cold dry THF (10 mL). The filtrate was cooled to 0° C. in a round bottom flask, followed by addition of NaOH (2.6 g, 65.23 mmol) solution in water (10 ml, 2.0 V) at 0° C. to 5° C. under nitrogen atmosphere. The reaction mixture was allowed to stir at 5° C. for 30 minutes and at room temperature for 2.0 h. The solvents were removed under reduced pressure at 30° C. The aqueous phase pH was adjusted to pH 2-3 using 1.5 N HCl solution. The aqueous phase was extracted with ethyl acetate (3×100 ml) and the combined organic phase was dried over Na$_2$SO$_4$, filtered and reduced under pressure at 30° C. to afford 1.2 g colorless oily liquid.

Step 2: Acetyl chloride (0.1 g, 1.29 mmol) was added to a solution of n-butyl dihydrogen phosphate (0.2 g, 1.42 mmol), triethyl amine (0.26 g, 2.59 mmol) and tetrahydrofuran (THF) (5.0 ml) at ambient temperature under nitrogen atmosphere. The reaction mixture was allowed to stir at 65° C. for 6.0 h. The reaction mixture was cooled to room temperature and concentrated under pressure to get white gummy solid with quantitative yield (not corrected for purity).

$^1$H NMR (400 MHz, CDCl$_3$) δ 0.80-0.90 (m, 3H), 1.50-1.65 (m, 4H), 2.06 (s, 3H), 3.93 (q, J=6.8 Hz, 2H) $^{31}$P (160 MHz, CDCl$_3$) δ−8.1, LC-MS (M−H) 194.9 at 0.5 minutes.

Example 3

Synthesis of Embodiment of Formula I

Compounds of general Formula I, where X is OH, may be prepared according to the procedure shown in Scheme 3, using the applicable R—OH as a starting compound. In the pathway shown below, the starting compound is n-butanol.

Scheme 3

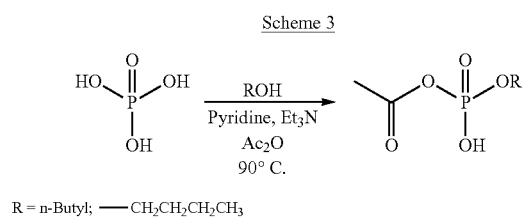

R = n-Butyl; ———CH₂CH₂CH₂CH₃

Phosphoric acid is reacted with alcohol in the presence of acetic anhydride activating agent, pyridine and triethylamine to yield acetic (alkyl phosphoric) anhydride.

Example 4

Antibacterial and Anti-Biofilm Activity of Compounds

Antibacterial and antibiofilm assay were performed on human pathogens and industrial microorganisms associated with contamination: *Staphylococcus aureus* (ATCC 25923 and ATCC 12600), *S. epidermidis* (ATCC 12228 and ATCC 14990), *Pseudomonas aeruginosa* (ATCC 27853), *E. coli* (ATCC 25922), *C. albicans* ATCC 18804), oral flora bacteria *Streptococcus mutans* (ATCC 25175) and *S. gordonii* (ATCC 33399), and/or marine biofilm former *Cobetia marina* (ATCC 25374).

Antibacterial assays were performed on planktonic bacteria to determine the Minimum Inhibitory Concentrations (MICs) and Minimum Bactericidal Concentrations (MBCs) for the compounds. MICs are defined as the lowest concentration of an antimicrobial that will inhibit the visible growth of a microorganism after overnight incubation. The MICs were determined using the standard CLSI Method M07-A9 for Dilution Antimicrobial Susceptibility Tests for Bacteria That Grow Aerobically modified for 96 well plates. MBCs are the lowest concentration of antimicrobial that kill the organism. MBCs were determined using the standard CLSI Method M26-A for Determining Bactericidal Activity of Antimicrobial Agents modified for 96 well plates.

Antibiofilm assays were performed to determine the prevention and removal of biofilm. The 96-well microplate assay was used to determine the Minimum Biofilm Inhibition Concentration (MBIC) (Merritt, et al. 2005. Growing and analyzing static biofilms. Curr Protoc Microbiol. Chapter 1, Unit 1.)

The MBIC assay is defined as the lowest concentration of the compound that will inhibit the biofilm. The ASTM E2799-12 Standard Test Method for Testing *Pseudomonas* Biofilm using the Minimum Biofilm Eradicating Concentration (MBEC) assay was used to determine biofilm removal. The MBEC assay is defined as the lowest concentration of compound that will eradicate the biofilm. The qualitative MBEC is determined using a microplate reader at absorbance 630 nm and the quantitative MBEC is determined using $\log_{10}$ reduction.

A selection of the compounds were used in the above assays against *S. aureus* (ATCC 25923). The results are provided in Table 6.

TABLE 6

Summary of antibacterial and antibiofilm activity of Formula 1 compounds against *S. aureus* ATCC 25923.

| Formula 1 Compound | MIC (% w/v) | MBC (% w/v) | MBIC (% w/v) | MBEC (% w/v) |
|---|---|---|---|---|
| X is NH₂; A is (CH₂)₃CH₃ | 0.25 | 0.25 | 0.25 | 0.25 |
| X is NH₂; A is (CH2)₂CH₃ | 1.16 | 1.16 | 1.16 | >2.3 |
| X is NH₂; A is C(CH₃)₃ | 1.0 | >1.0 | 1.0 | >2.3 |
| X is OH; A is (CH₂)₃CH₃ | 1.69 | 1.69 | 1.69 | >2.3 |
| X is OH; A is (CH₂)₂CH₃ | 2.25 | >2.3 | 2.25 | >2.3 |
| X is OH; A is CH(CH₃)₂ | >2.3 | >2.3 | >2.3 | 2.3 |
| X is OH; A is C(CH₃)₃ | 2.23 | >2.23 | 2.23 | 2.23 |
| X is OH; A is (CH₂)₄CH₃ | >2.3 | >2.3 | >2.3 | 2.3 |

MIC = minimum inhibitory concentration;
MBC = minimum bactericidal concentration;
MBIC = minimum biofilm inhibiting concentration;
MBEC = minimum biofilm eradicating concentration.

In brief, the compounds inhibited the growth of the target microorganisms 99.99% (p<0.01) (Table 6). The compounds prevented biofilm formation by the target microorganisms up to 99.99% (p<0.01) (Table 6). The compounds removed existing biofilm formed by the target microorganisms 99.99% (p<0.01) (Table 6). Quantitative MBEC $\log_{10}$ reduction ranged from 3.9 to 4.4 (data not shown). Table 6 shows a summary of antibacterial and antibiofilm activity of a select number of tested compounds against *S. aureus* ATCC 25923. The activity of the compounds against the other target biofilm formers showed similar results.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A compound of Formula I, or a salt thereof, wherein Formula I is represented by the structure:

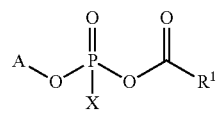

where A is $C_{1-10}$ hydrocarbyl or optionally $R^1$ substituted $C_{1-10}$ hydrocarbyl; X is —NHR, —NHOR, —NHCOR, or —NHOCOR; and R is H;

$R^1$ is selected from hydrogen, halogen, cyano, OH, $C_{1-6}$ alkyl, $C_{1-6}$ alkoxy, $SOR^2$, $SO_2R^2$, $SO_2NR^3R^4$, $COR^2$, $CO_2R^2$, $CONR^3R^4$, $NR^3R^4$, $NR^3COR^4$, $NR^3SO_2R^4$, $NR^3CO_2R^4$, $NR^3CONR^4$, $OCOR^2$, and phosphonic acid, wherein each of $C_{1-6}$ alkyl, $C_{1-6}$ alkoxy, $SOR^2$, $SO_2R^2$, $SO_2NR^3R^4$, $COR^2$, $CO_2R^2$, $CONR^3R^4$, $NR^3R^4$, $NR^3COR^4$, $NR^3SO_2R^4$, $NR^3CO_2R^4$, $NR^3CONR^4$, $OCOR^2$, can be optionally substituted with halo, amino, hydroxyl, $C_{1-6}$ alkyl, $C_{1-6}$ alkoxy, cyano, or phosphonic acid;

$R^2$, $R^3$, and $R^4$ are independently selected from hydrogen, $C_{1-6}$ hydrocarbyl, in which each of the $C_{1-6}$ hydrocarbyl can be optionally substituted with halo, amino, hydroxyl, $C_{1-6}$ alkoxy, cyano, or phosphonic acid.

2. The compound of Formula I of claim 1, wherein A is $C_{3-5}$ alkyl, $R^1$ is $CH_3$, and X is $NH_2$.

3. The compound of Formula I of claim 2, wherein the compound is selected from the group consisting of:

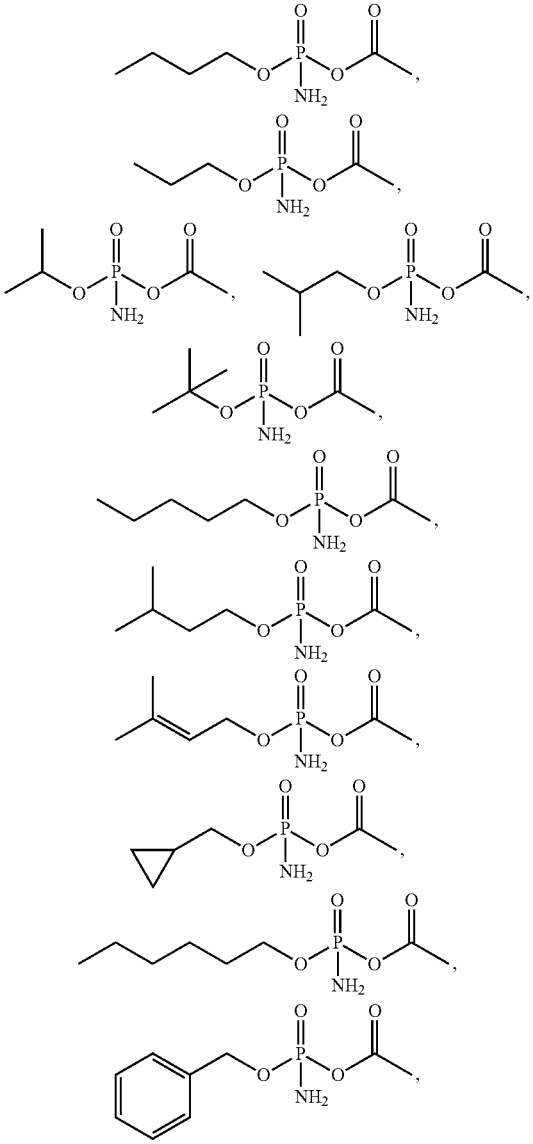

-continued

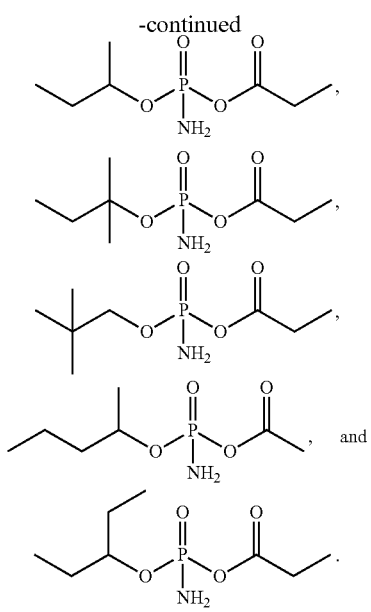

4. The compound of Formula I of claim 3, wherein the compound is:

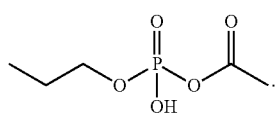

5. The compound of Formula I of claim 3, wherein the compound is:

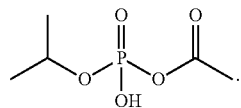

6. The compound of Formula I of claim 3, wherein the compound

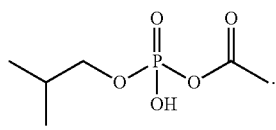

7. The compound of Formula I of claim 3, wherein the compound is:

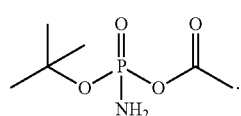

8. The compound of Formula I of claim 3, wherein the compound

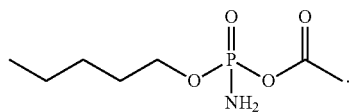

9. A composition comprising a compound of claim 1.

10. A method of dispersing or inhibiting the growth of a biofilm, or inhibiting the growth of, or killing a fungus or bacteria, comprising contacting the biofilm, fungus or bacteria with an amount of a compound of Formula I of claim 1, or a composition comprising an amount of a compound of Formula I, wherein the amount of the compound of Formula I is effective to disperse or inhibit the growth of the biofilm, or inhibit the growth of or kill the fungus or bacteria.

11. The method of claim 10, wherein the compound of Formula I is represented by the structure:

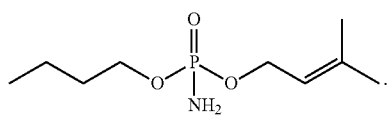

12. A method of treating a surface with a compound of Formula I of claim 1 comprising contacting the surface with an amount of a compound of Formula I effective to treat the surface, wherein the compound of Formula I acts as a cleaning agent, dispersant, surfactant, biofilm removal agent, or antibiofilm, antifouling, antimicrobial, or antifungal agent.

13. The method of claim 12, wherein the compound of Formula I is represented by the structure:

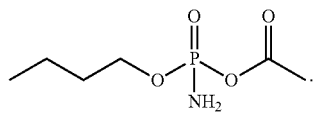

14. The compound of Formula I of claim 3, wherein the compound is:

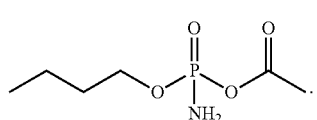

* * * * *

UNITED STATES PATENT AND TRADEMARK OFFICE
CERTIFICATE OF CORRECTION

PATENT NO. : 11,457,631 B2  
APPLICATION NO. : 16/311294  
DATED : October 4, 2022  
INVENTOR(S) : Cynthia K. Burzell et al.

Page 1 of 1

It is certified that error appears in the above-identified patent and that said Letters Patent is hereby corrected as shown below:

In the Claims

Claim 4, compound should read:

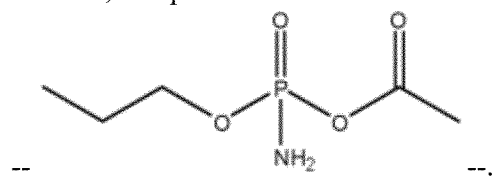

-- --.

Claim 5, compound should read:

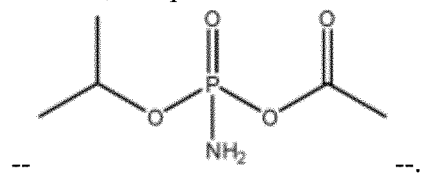

-- --.

Claim 6, compound should read:

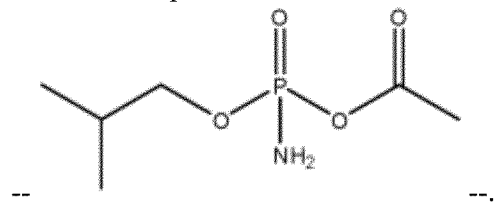

-- --.

Signed and Sealed this  
Twelfth Day of August, 2025

Coke Morgan Stewart  
*Acting Director of the United States Patent and Trademark Office*